United States Patent [19]

Schally et al.

[11] Patent Number: 6,057,422

[45] Date of Patent: May 2, 2000

[54] ANTAGONISTIC ANALOGS OF GH-RH INHIBITING IGF-I AND -II

[75] Inventors: Andrew V. Schally, Metairie; Jozsef Varga, New Orleans, both of La.; Marta Zarandi, Szeged H., Hungary

[73] Assignee: The Administrators of the Tulane Educational Fund, New Orleans, La.

[21] Appl. No.: 09/199,381

[22] Filed: Nov. 25, 1998

[51] Int. Cl.[7] .............................. C07K 7/64; C07K 7/00; C07K 11/00; A61K 38/16; A61K 38/25

[52] U.S. Cl. .............................. 530/324; 530/317; 514/9; 514/11; 514/12; 436/64

[58] Field of Search .................................. 514/9, 11, 12, 514/530; 530/317, 324; 436/64

[56] References Cited

U.S. PATENT DOCUMENTS 5,550,212  8/1996  Zanandi et al. .......................... 530/324
5,942,489  8/1999  Schally et al. ............................ 514/11

FOREIGN PATENT DOCUMENTS

91/16923  11/1991  WIPO .
97/42223  11/1997  WIPO .

OTHER PUBLICATIONS

Zanandi et al, "Synthesis and Biological Activities of Highly Potent Antagonists of Growth Hormone–Releasing Hormone" Proc. Natl. Acad. Sci., USA, vol. 91, pp. 22298–12302, Dec. 1994.

*Primary Examiner*—F. T. Moezie
*Attorney, Agent, or Firm*—Omri M. Behr, Esq.

[57] ABSTRACT

There is provided a novel series of synthetic analogs of hGH-RH(1-29) $NH_2$. These analogs inhibit the activity of endogenous hGH-RH, and therefore prevent the release of growth hormone. The stronger inhibitory potencies of the new analogs, as compared to previously described ones, results from replacement of various amino acids.

8 Claims, 5 Drawing Sheets

Antitumor Effects of GH-RH Antagonists Peptide 1, Peptide 3, and MZ-5-156 on MXT Mouse Mammary Cancers Antitumor Effects of GH-RH Antagonists Peptide 1, and MZ-5-156 on MDA-MB-468 Human Breast Cancer Xenografts in Nude Mice Antitumor Effects of GH-RH Antagonists Peptide 1, Peptide 9, Peptide 11, MZ-4-71, and MZ-5-156 on HT-29 Human Colon Cancer Xenografts in Nude Mice Antitumor Effect of GH-RH Antagonist Peptide 1 on U87MG Human Glioblastoma Xenografts in Nude Mice Antitumor Effects of GH-RH Antagonists Peptide 3, and MZ-5-156 on PC-3 Human Prostate Cancer Xenografts in Nude Mice \* p= 0.056
\*\* p= 0.013

6,057,422

ANTAGONISTIC ANALOGS OF GH-RH INHIBITING IGF-I AND -II

FIELD OF INVENTION

This invention was made in part with Government support from the Medical Research Service of the Veterans Affairs Department. The Government has certain rights in this application.

The present invention relates to novel synthetic peptides which inhibit the release of growth hormone from the pituitary in mammals, and to therapeutic compositions containing these novel peptides.

BACKGROUND OF THE INVENTION

Growth Hormone ("GH") is a peptide having 191 amino acids which stimulates the production of numerous different growth factors, e.g. insulin-like growth factor I (IGF-I) and so promotes growth of numerous tissues (skeleton, connective tissue, muscle and viscera) and physiological activities (raising nucleic acid and protein synthesis and lipolysis, but lowering urea secretion).

Release of GH is under the control of releasing and inhibiting factors secreted by the hypothalamus. The primary releasing factor is growth hormone releasing hormone ("GH-RH"); human growth hormone-releasing hormone ("hGH-RH") is a peptide having 44 amino acids. The novel peptides of the present invention relate to analogues of hGH-RH having only residues 1 through 29 ("hGH-RH(1-29)NH$_2$"), i.e., to analogues of the peptide which has the amino acid sequence:

Tyr-Ala-Asp-Ala-Ile$_5$-Phe-Thr-Asn-Ser-Tyr$^{10}$-Arg-Lys-Val-Leu-Gly$_{15}$-Gln-Leu-Ser-Ala-Arg$^{20}$-Lys-Leu-Leu-Gln-Asp$^{25}$-Ile-Met-Ser-Arg$^{29}$-NH$_2$

GH has been implicated in several diseases. One disease in which GH is involved is acromegaly, in which excessive levels of GH are present. The abnormally enlarged facial and extremity bones of this disease can be treated by administering a GH-RH antagonist.

Further diseases involving GH are diabetic retinopathy and diabetic nephropathy. The damage to the retina and kidneys respectively in these diseases, believed to be due to GH, results in blindness or reduction in kidney function. This damage can be prevented or slowed by administration of an effective GH-RH antagonist.

However, the main applications of GH-RH antagonists would be in the field of cancer (A. V. Schally et al, in *Growth Hormone Secretagogues in Clinical Practice*, eds. Bercu, B. B. & Walker, R. F., Dekker, New York, pp. 145–162, 1998). IGF-I and -II are potent mitogens for various cancers. By suppressing GH secretion, GH-RH antagonists decreases the synthesis of IGF-I in the liver and other tissues. GH-RH antagonists also reduce the autocrine and paracrine production of IGF-I and/or IGF-II by various tumors. In several experimental cancers, treatment with antagonists of GH-RH produces a reduction in IGF-I and -II, concomitant to inhibition of tumor growth.

In an effort to intervene in these disease and other conditions, some investigators have attempted to control GH levels by using somatostatin, one inhibitor of GH release. However, somatostatin, if administered alone, does not suppress GH or IGF-I levels to a desired degree. If administered in combination with a GH-RH antagonist, somatostatin would improve suppression of IGF-I levels much better.

Scientists have investigated various modifications of GH-RH to elucidate the relationship of the structure of GH-RH to its activity in an effort to provide synthetic congeners with improved agonistic or antagonistic properties. Thus, it was early established that GH-RH fragment comprising residues 1 to 29, or GH-RH(1-29), is the minimum sequence necessary for biological activity. This fragment retains 50% or more of the potency of native GH-RH.

The first described GH-RH antagonist, [Ac-Tyr$^1$, D-Arg$^2$] hGH-RH(1-29) NH$_2$, which is generally termed as the "standard antagonist" in the literature, was found to prevent the activation of rat anterior pituitary adenylate cyclase by hGH-RH(1-29)NH$_2$. The same peptide blocked the action of GH-RH on its receptors in the pituitary and hypothalamus, and inhibited the pulsatile growth hormone secretion.

A considerable number of patents and articles in the open literature disclose analogs of GH-RH which either act as agonists of GH-RH (i.e. act to stimulate the release of GH) or as antagonists of GH-RH (i.e. act to inhibit the release of GH). Most of these peptides are derived from the GH-RH (1-29) peptide sequence, with specific structural modifications which account for their enhanced agonistic or antagonistic properties.

Thus, U.S. Pat. No. 4,659,693 discloses GH-RH antagonistic analogs which contain certain N,N'-dialkyl-omega-guanidino alpha-amino acyl residues in position 2 of the GH-RH(1-29) sequence.

Published application WO 91/16923 reviews earlier attempts to alter the secondary structure of hGH-RH by modifying its amino acid sequence. These earlier attempts include: replacing Tyr$^1$, Ala$^2$, Asp$^3$ or Asn$^8$ with their D-isomers; replacing Asn$^8$ with L- or D-Ser, D-Arg, Asn, Thr, Gln or D-Lys; replacing Ser$^9$ with Ala to enhance amphiphilicity of the region; and replacing Gly$^{15}$ with Ala or Aib. When R$^2$ in the analogs is D-Arg, and R$^8$, R$^9$, and R$^{15}$ are substituted as indicated above, antagonistic activity is said to result. These antagonistic peptides are said to be suitable for administration as pharmaceutical compositions to treat conditions associated with excessive levels of GH, e.g., acromegaly.

The antagonistic activity of the hGH-RH analogue "[Ser$^9$-Ψ[CH$_2$-NH]-Tyr$^{10}$]hGH-RH(1-29)" of U.S. Pat. No. 5,084,555 was said to result from the pseudopeptide bond (i.e., a peptide bond reduced to a [CH$_2$-NH] linkage) between the R$^9$ and R$^{10}$ residues. However, the antagonistic properties of [Ser$^9$-Ψ[CH$_2$-NH]-Tyr$^{10}$]hGH-RH(1-29)were said to be inferior to the standard antagonist, [N-Ac-Tyr$^1$, D-Arg$^2$]GH-RH(1-29)-NH$_2$.

U.S. Pat. No. 5,550,212, and U.S. patent application Ser. No. 08/642,472, assigned to the same assignee as the present application, disclose analogs of hGH-RH(1-29)NH$_2$ said to have enhanced antagonistic properties and prolonged duration of action. These properties are believed to result from replacement of various amino acids and acylation with aromatic or nonpolar acids at the N-terminus of GH-RH(1-29)NH$_2$. It is noted that in the above U.S. patent and U.S. patent application, R$^9$ is always Ser, R$^{16}$ is Gln or an amino acid forming a lactam bridge (i.e. Glu), R$^{28}$ is Ser, Asn, Asp, Ala or Abu, and R$^{29}$ is Agm, Arg-NH$_2$, Arg-OH, Cit-NH$_2$, Cit-OH, Har-NH$_2$, Har-OH, or an amino acid forming a lactam bridge (i.e. Lys or Orn).

SUMMARY OF THE INVENTION

There is provided a novel series of synthetic analogs of hGH-RH(1-29) NH$_2$. These analogs inhibit the activity of endogenous hGH-RH, and therefore prevent the release of growth hormone. The stronger inhibitory potencies of the new analogs, as compared to previously described ones, results from replacement of various amino acids.

Specifically, the invention relates to peptides comprising the formulae: X-R$_1$-R$^2$-Asp-Ala-R$^5$-R$^6$-Thr-R$^8$-R$^9$-R$^{10}$-Arg- $R^{12}$-$R^{13}$-$R^{14}$-$R^{15}$-$R^{16}$-Leu-$R^{18}$-$R^{19}$-Arg-$R^{21}$-$R^{22}$-Leu-Gln-Asp-Ile-$R^{27}$-$R^{28}$-$R^{29}$-$NH_2$ wherein X is PhAc, IndAc, Ibu, Nac, 1- or 2-Npr, or Fpr, $R^1$ is Tyr or His, $R^2$ is D-Arg or D-Cit, $R^5$ is Ile or Val, $R^6$ is Phe, Nal or Phe(Y), in which Y=F, Cl, Br, $R^8$ is Asn, Gln, Ser, Thr, Ala, D-Asn, D-Gln, D-Ser, D-Thr, Abu, D-Abu, or Aib, $R^9$ is Arg, Har, Lys, Orn, D-Arg, D-Har, D-Lys, D-Orn, Cit, Nle, Tyr (Me), Ser, Ala or Aib, $R^{10}$ is Tyr or Phe(Y), in which Y=H, F, Cl, Br, or $OCH_3$, $R^{12}$ is Lys, D-Lys, or Orn, $R^{13}$ is Val or Nle, $R^{14}$ is Leu or Nle, $R^{15}$ is Gly, Ala, Abu, Nle or Gin, $R^{16}$ is Gln or Arg, $R^{18}$ is Ser or Nle, $R^{19}$ is Ala or Abu, $R^{21}$ is Lys or Orn, $R^{22}$ is Leu, Ala or Aib, $R^{27}$ is Met, Leu, Nle, Abu, or D-Arg, $R^{28}$ is Arg, D-Arg, Ser, Asn, Asp, Ala or Abu, $R^{29}$ is Arg, D-Arg, Har or D-Har, and pharmaceutically acceptable salts thereof.

Among the preferred embodiment are peptides wherein X is PhAc, IndAc or Nac, $R^1$ is Tyr or His, $R^2$ is D-Arg, $R^5$ is Ile, $R^6$ is Phe(pCl), $R^8$ is Asn or Abu, $R^9$ is Arg or Har, Lys, Orn, D-Arg, D-Har, D-Lys, D-Orn, Cit, Nle, or Tyr (Me), $R^{10}$ is Tyr or Tyr(Me), $R^{12}$ is Lys, $R^{13}$ is Val or Nle, $R^{14}$ is Leu or Nle, $R^{15}$ is Abu, Ala, or Nle, $R^{16}$ is Gln or Arg, $R^{18}$ is Ser or Nle, $R^{19}$ is Ala or Abu, $R^{21}$ is Lys, $R^{27}$ is Nle or D-Arg,, $R^{28}$ is D-Arg, Arg, or Ser, $R^{29}$ is D-Arg, Har or D-Har.

It is noted that the amino acid residues from 30 through 44 of the native GH-RH molecule do not appear to be essential to activity; nor does their identity appear to be critical. Therefore, it appears that the addition of some or all of these further amino acid residues to the C-terminus of the hGH-RH(1-29)-$NH_2$ analogues of the present invention will not affect the efficacy of these analogues as GH-RH antagonists. If some or all of these amino acids were added to the C-terminus of the hGH-RH(1-29)-$NH_2$ analogues, the added amino acid residues could be the same as residues 30 through 44 in the native hGH-RH sequence or reasonable equivalents.

Synthetic Methods

The synthetic peptides are synthesized by a suitable method such as by exclusive solid phase techniques, by partial solid-phase techniques, by fragment condensation or by classical solution phase synthesis.

When the analogues of this invention are synthesized by solid-phase method, the C-terminus residue (here, $R^{29}$) is appropriately linked (anchored) to an inert solid support (resin) while bearing protecting groups for its alpha amino group (and, where appropriate, for its side chain functional group). After completion of this step, the alpha amino protecting group is removed from the anchored amino acid residue and the next amino acid residue, $R^{28}$, is added having its alpha amino group (as well as any appropriate side chain functional group) suitably protected, and so forth. The N-terminus protecting groups are removed after each residue is added, but the side chain protecting groups are not yet removed. After all the desired amino acids have been linked in the proper sequence, the peptide is cleaved from the support and freed from all side chain protecting group(s) under conditions that are minimally destructive towards residues in the sequence. This is be followed by a careful purification and scrupulous characterization of the synthetic product, so as to ensure that the desired structure is indeed the one obtained.

It is particularly preferred to protect the alpha amino function of the amino acids during the coupling step with an acid or base sensitive protecting group. Such protecting groups should have the properties of being stable in the conditions of peptide linkage formation, while being readily removable without destruction of the growing peptide chain and without racemization of any of the chiral centers contained therein. Suitable alpha amino protecting groups are Boc and Fmoc.

Medical Applications

The hGH-RH antagonist peptides, or salts of these peptides, may be formulated in pharmaceutical dosage forms containing effective amounts thereof and administered to humans or animal for therapeutic or diagnostic purposes. The peptides may be used to suppress GH levels and to treat conditions associated with excessive levels of GH, e.g., diabetic retinopathy and nephropathy, and acromegaly. Also provided are methods for treating these diseases by administration of a composition of the invention to an individual needing such treatment. The main uses of GH-RH antagonists are however,in the field of cancer, for example human cancers of the breast, lung, colon, brain, pancreas, and prostate where the receptors for IGF-I or IGF-II are present.

BRIEF DESCRIPTION OF THE DRAWINGS

FIG. I is a plot of volume changes of MXT mouse mammary cancers during treatment with certain GH-RH antagonists against days of treatment.

FIG. II is a plot of volume changes of MDA-MB-468 human breast cancers in nude mice during treatment with certain GH-RH antagonists against days of treatment.

Figure 1:
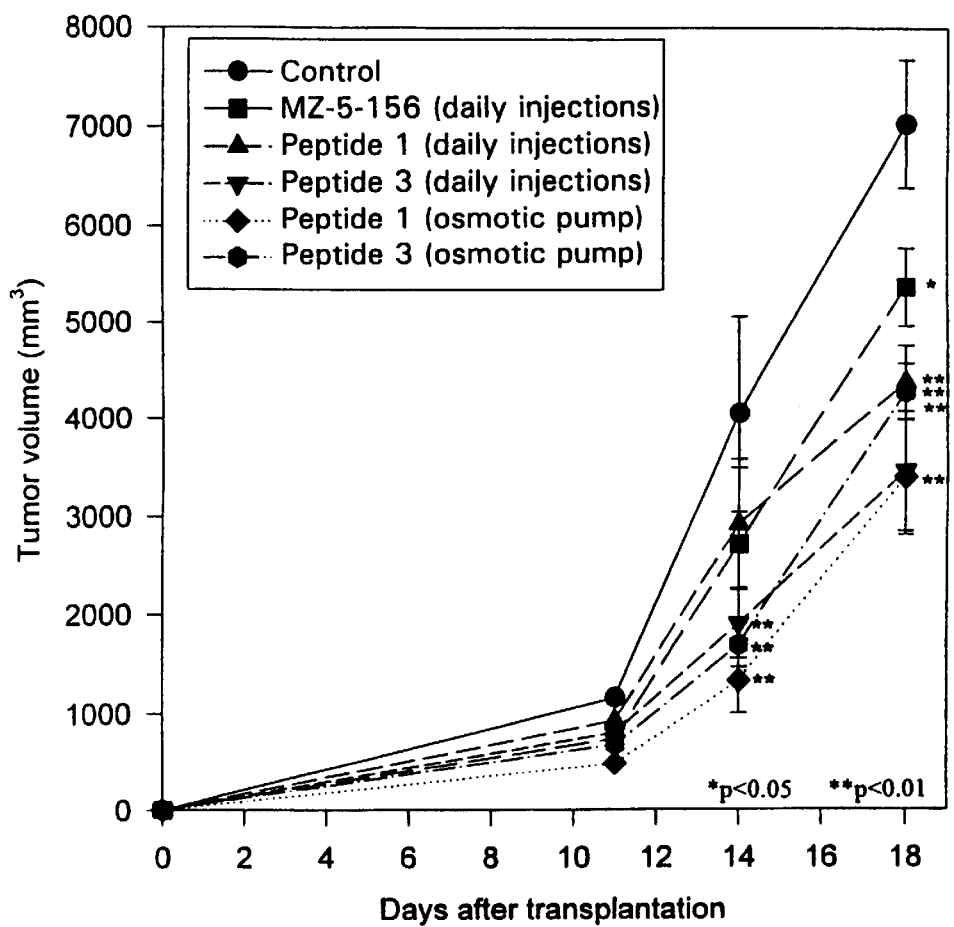
Figure 2:
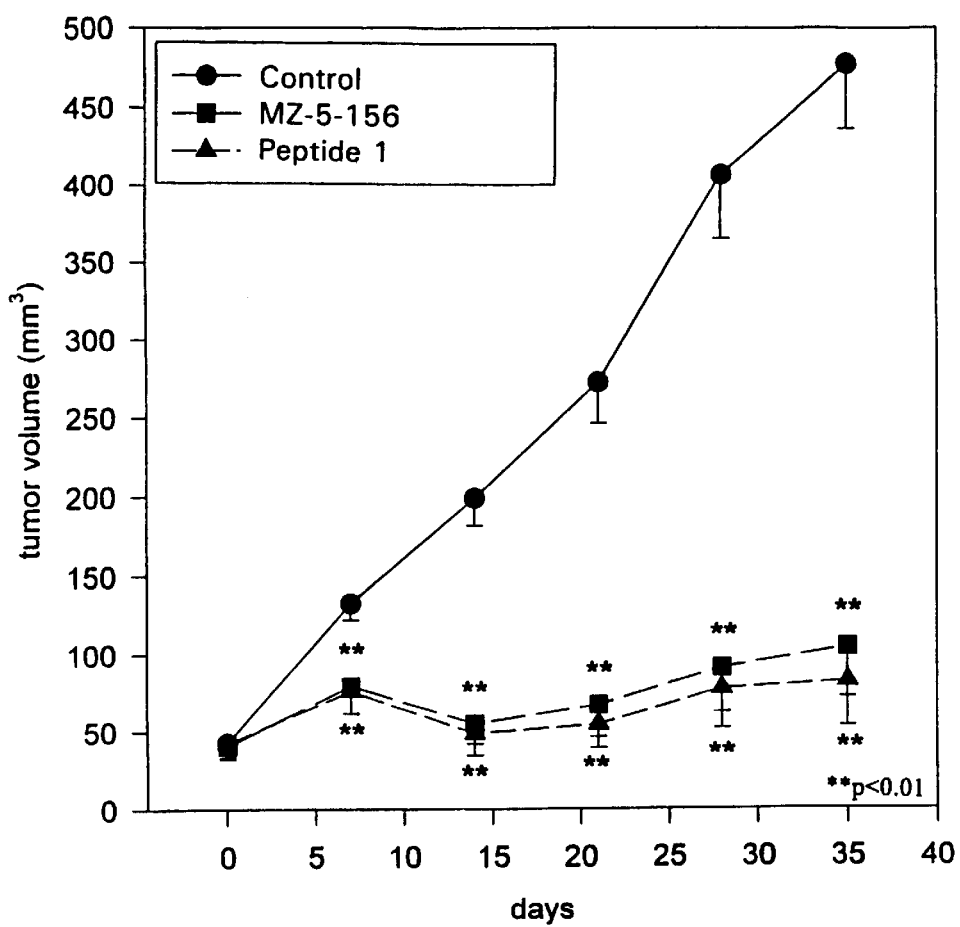
Figure 3:
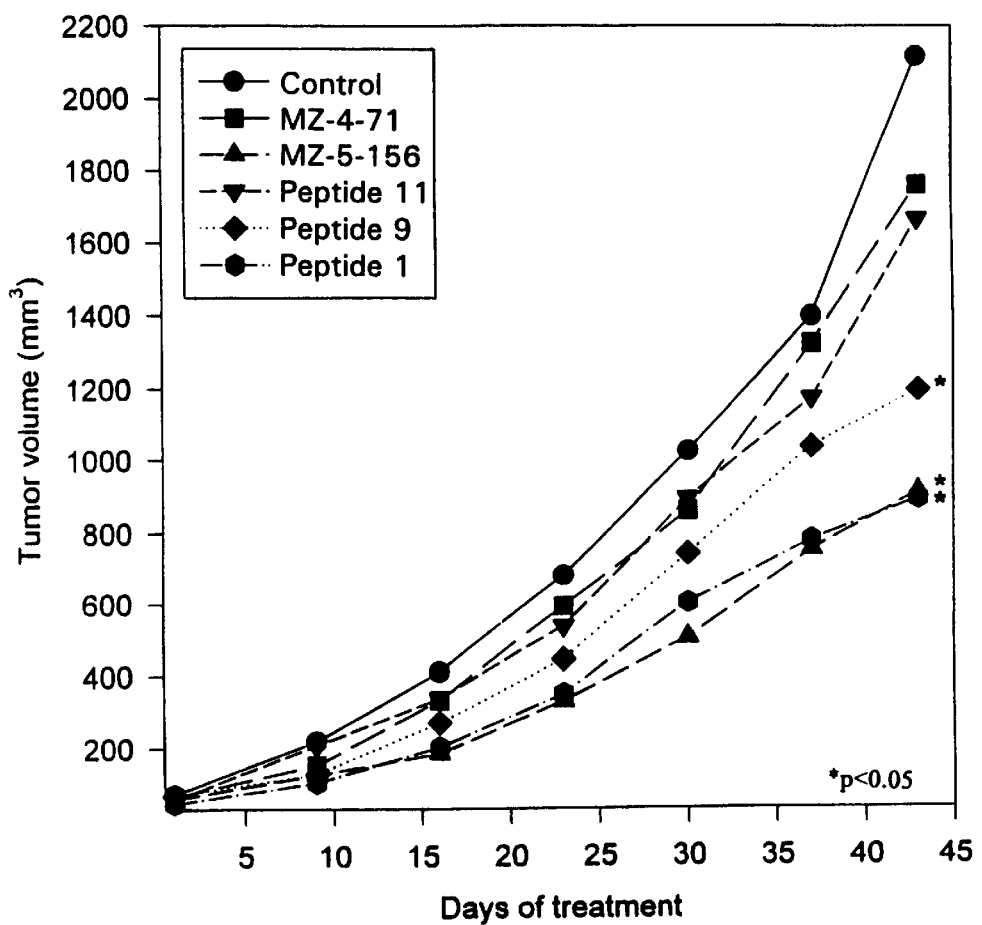
Figure 4:
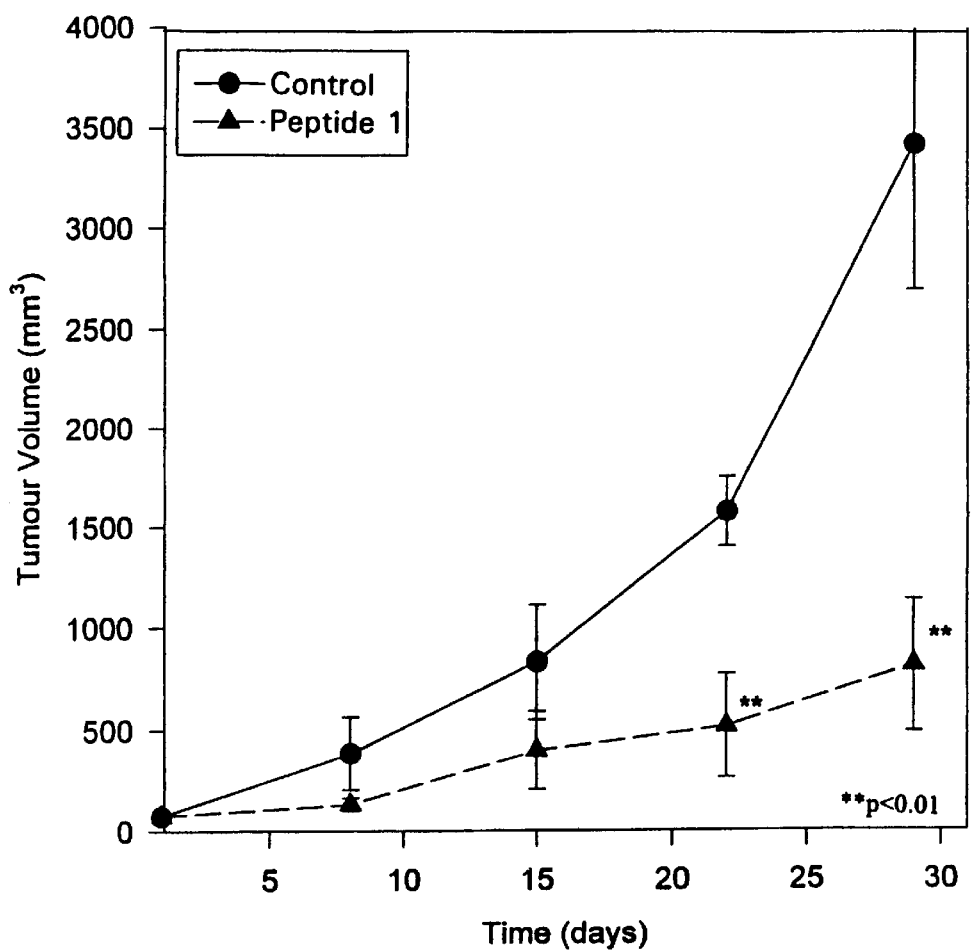
Figure 5:
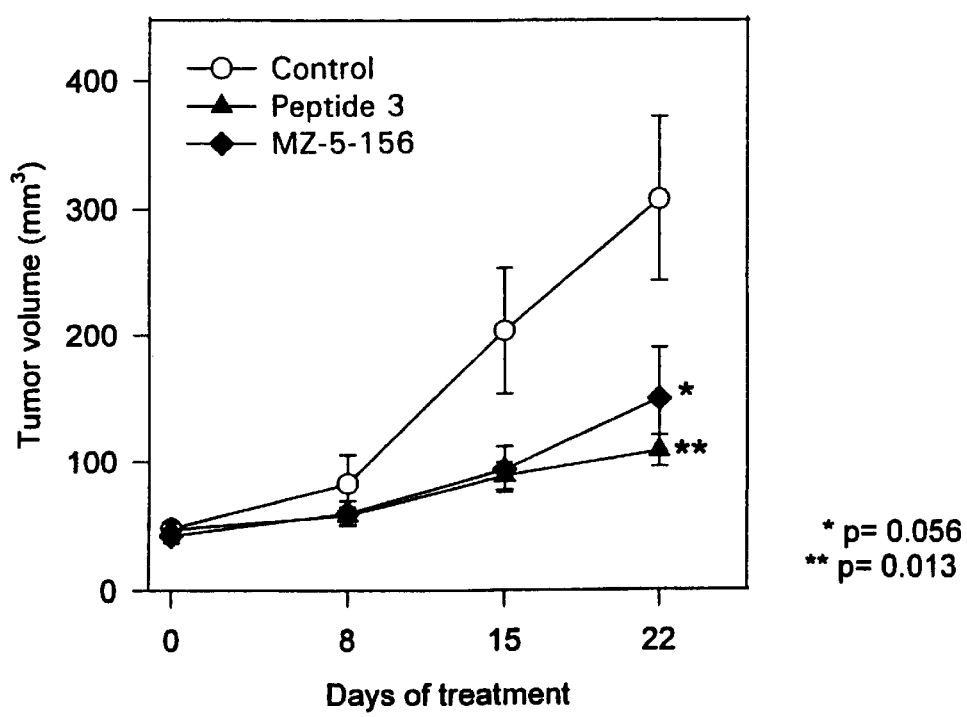

FIG. III is a plot of volume changes of HT-29 human colon cancers in nude mice during treatment with certain GH-RH antagonists against days of treatment.

FIG. IV is a plot of volume changes of U87MG human glioblastomas in nude mice during treatment with a GH-RH antagonist against days of treatment.

FIG. V is a plot of volume changes of PC-3 human prostate cancers in nude mice during treatment with certain GH-RH antagonists against days of treatment.

DETAILED DESCRIPTION OF THE PREFERRED EMBODIMENTS

A. Abbreviations

The nomenclature used to define the peptides is that specified by the IUPAC-IUB Commissioner on Biochemical Nomenclature wherein, in accordance with conventional representation, the amino group at the N-terminus appears to the left and the carboxyl group at the C-terminus appears to the right. The term "natural amino acid" as used herein means one of the common, naturally occurring L-amino acids found in naturally occurring proteins: Gly, Ala, Val, Leu, Ile, Ser, Thr, Lys, Arg, Asp, Asn, Glu, Gln, Cys, Met Phe, Tyr, Pro, Trp and His. When the natural amino acid residue has isomeric forms, it is the L-form of the amino acid that is represented herein unless otherwise expressly indicated.

Non-coded amino acids, or amino acid analogues, are also incorporated into the GH-RH antagonists. ("Non-coded" amino acids are those amino acids which are not among the approximately 20 natural amino acids found in naturally occurring peptides.) Among the non-coded amino acids or amino acid analogues which may be used in the hGH-RH antagonist peptides are the following: by Abu is meant alpha amino butyric acid, by Aib is meant alpha amino isobutyric acid, by Har is meant homoarginine, by Nal is meant 2-naphthyl-alanine, by Nle is meant norleucine, and by Orn is meant ornithine. When these non-coded amino acids, or amino acid analogues, have isomeric forms, it is the L-form of the amino acid that is represented unless otherwise expressly indicated.

Abbreviations used herein are:

| | |
|---|---|
| Abu | α-aminobutyric acid |
| Ac | acetyl |
| AcOH | acetic acid |
| Ac$_2$O | acetic anhydride |
| Aib | α-aminoisobutyric acid |
| Boc | tert.butyloxycarbonyl |
| Bom | benzyloxymethyl |
| 2BrZ | 2-bromo-benzyloxycarbonyl |
| cHx | cyclohexyl |
| Cit | citrulline (2-amino-5-ureidovaleric acid) |
| 2ClZ | 2-chloro-benzyloxycarbonyl |
| DCM | dichloromethane |
| DIC | N,N'-diisopropylcarbodiimide |
| DIEA | diisopropylethylamine |
| DMF | dimethylformamide |
| Fmoc | fluorenylmethyloxycarbonyl |
| Fpr | 3-phenylpropionyl |
| GH | growth hormone |
| GH-RH | GH releasing hormone |
| Har | homoarginine |
| HBTU | 2-(1H-Benzotriazol-1-yl)-1,1,3,3-tetramethyluronium hexaflourophosphate |
| hGH-RH | human GH-RH |
| HOBt | 1-hydroxybenzotriazole |
| HPLC | high performance liquid chromatography |
| Ibu | isobutyryl |
| IndAc | indole-3-acetyl |
| MBHA | para-methylbenzhydrylamine |
| MeOH | methanol |
| MeCN | acetonitrile |
| Nac | 1-naphthylacetyl |
| Nal | 2-naphthylalanine |
| NMM | N-methylmorpholine |
| Npr | naphthylpropionyl |
| PAM | phenylacetamidomethyl |
| Phe(pCl) | para-chloro-phenylalanine |
| PhAc | phenylacetyl |
| rGH-RH | rat GH-RH |
| RP-HPLC | reversed phase HPLC |
| TFA | trifluoroacetic acid |
| Tos | para-toluenesulfonyl |
| Tyr(Me) | tyrosine methylether |
| Z | benzyloxycarbonyl |

B. The GH-RH Analogs

The hGH-RH analogues of the present invention were designed to increase the affinities of the peptides to the receptor, to improve metabolic stability and to maximize the amphiphilic secondary structure of the molecules. Many of these analogues cause very effective and long lasting inhibition of the GH release stimulated by hGH-RH(1-29)NH$_2$ in vitro and in vivo.

The following embodiments are specially preferred as having remarkable bioactivity:

[PhAc$^0$, D-Arg$^2$, Phe(pCl)$^6$, Arg$^9$, Abu$^{15}$, Nle$^{27}$, D-Arg$^{28}$, Har$^{29}$]hGH-RH(1-29) NH$_2$ Peptide 1

[IndAc$^0$, D-Arg$^2$, Phe(pCl)$^6$, Arg$^9$, Abu$^{15}$, Nle$^{27}$, D-Arg$^{28}$, Har$^{29}$]hGH-RH(1-29) NH$_2$ Peptide 2

[PhAc$^0$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NH$_2$ Peptide 3

[PhAc$^0$, D-Arg$^2$, Phe(pCl)$^6$, Har$^9$, Abu$^{15}$, Nle$^{27}$, D-Arg$^{28}$, Har$^{29}$]hGH-RH(1-29) NH$_2$ Peptide 4

[Nac$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 5

[PhAc$^0$, D-Arg$^2$, Phe(pCl)$^6$, Arg$^9$, Tyr(Me)$^{10}$, Abu$^{15}$, Nle$^{27}$, D-Arg$^{28}$, Har$^{29}$]hGH-RH(1-29)NH$_2$ Peptide 6

[PhAc$^0$, His$^1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 7

[Nac$^0$, His$^1$, D-Arg$^2$, Phe(pCl)$^6$ Arg$^9$, Abu$^{15}$, Nle$^{27}$, D-Arg$^{28}$, Har$^{29}$]hGH-RH(1-29)NH$_2$ Peptide 8

[PhAc$^0$, D-Arg$^2$, Phe(pCl)$^6$, Arg$^9$, Abu$^{15}$, Nle$^{27}$, D-Arg$^{29}$] hGH-RH(1-29)NH$_{Peptide}$ 9

[PhAc$^0$, D-Arg$^2$, Phe(pCl)$^6$, Abu$^{15}$, Arg$^{16}$, Nle$^{27}$, D-Arg$^{29}$] hGH-RH(1-29) NH$_2$ Peptide 10

[PhAc$^0$, D-Arg$^2$, Phe(pCl)$^6$, Abu$^{15}$, Nle$^{27}$, D-Arg$^{28}$, Har$^{29}$] hGH-RH (1-29)NH$_2$ Peptide 11

[PhAc$^0$, D-Arg$^2$, Phe(pCl)$^6$, Nle$^9$, Abu$^{15}$, Nle$^{27}$, D-Arg$^{29}$] hGH-RH(1-29) NH$_2$ Peptide 12

[PhAc$^0$, D-Arg$^2$, Phe(pCl)$^6$, Nle$^{13}$, Nle$^{14}$, Abu$^{15}$, Nle$^{27}$, D-Arg$^{29}$]hGH-RH(1-29)NH$_2$ Peptide 13

[PhAc$^0$, D-Arg$^2$, Phe(pCl)$^6$, Nle$^{15}$, Nle$^{27}$, D-Arg$^{29}$]hGH-RH (1-29)NH$_2$ Peptide 14

[PhAc$^0$, D-Arg$^2$, Phe(pCl)$^6$, Abu$^{15}$, Nle$^{18}$, Nle$^{27}$, D-Arg$^{29}$] hGH-RH (1-29)NH$_2$ Peptide 15

[PhAc$^0$, D-Arg$^2$, Phe(pCl)$^6$, Tyr(Me)$^{10}$, Abu$^{15}$, Nle$^{27}$, D-Arg$^{29}$]hGH-RH(1-29) NH$_2$ Peptide 16

[PhAc$^0$, D-Arg$^2$, Phe(pCl)$^6$, Abu$^8$, Tyr(Me)$^{10}$, Abu$^{15}$, Nle$^{27}$, D-Arg$^{29}$]hGH-RH (1-29)NH$_2$ Peptide 17

[PhAc$^0$, D-Arg$^2$, Phe(pCl)$^6$, D-Abu$^8$, Tyr(Me)$^{10}$, Abu$^{15}$, Nle$^{27}$, D-Arg$^{29}$]hGH -RH(1-29)NH$_2$ Peptide 18

[PhAc$^0$, D-Arg$^2$, Phe(pCl)$^6$, Tyr(Me)$^{10}$, Abu$^{15}$, D-Arg$^{27}$, Arg$^{28}$, D-Arg$^{29}$]hGH -RH(1-29)NH$_2$ Peptide 19

[PhAc$^0$, D-Arg$^2$, Phe(pCl)$^6$, Tyr(Me)$^9$, Abu$^{15}$, D-Arg$^{27}$, Arg$^{28}$, D-Arg$^{29}$]hGH-RH(1-29)NH$_2$ Peptide 20

[PhAc$^0$, D-Arg$^2$, Phe(pCl)$^6$, Abu$^{15}$, D-Arg$^{27}$, Arg$^{28}$, D-Arg$^{29}$]hGH-RH(1-29) NH$_2$ Peptide 21

[PhAc$^0$, D-Arg$^2$, Phe(pCl)$^6$, Abu$^8$, Tyr(Me)$^{10}$, Abu$^{15}$, D-Arg$^{27}$ Arg$^{28}$, D-Arg$^{29}$]hGH-RH(1-29)NH$_2$ Peptide 22

[PhAc$^0$, D-Arg$^2$, Phe(pCl)$^6$, D-Abu$^8$, Tyr(Me)$^{10}$, Abu$^{15}$, D-Arg$^{27}$, Arg$^{28}$, D-Arg$^{29}$]hGH-RH(1-29)NH$_2$ Peptide 23

[PhAc$^0$, D-Arg$^2$, Phe(pCl)$^6$, Lys$^9$, Abu$^{15}$, Nle$^{27}$, D-Arg$^{28}$, Har$^{29}$]hGH-RH(1-29)NH$_2$ Peptide 24

[PhAc$^0$, D-Arg$^2$, Phe(pCl)$^6$, D-Arg$^9$, Abu$^{15}$, Nle$^{27}$, D-Arg$^{28}$, Har$^{29}$]hGH-RH(1-29)NH$_2$ Peptide 25

[PhAc$^0$, D-Arg$^2$, Phe(pCl)$^6$, D-Arg$^9$, Abu$^{15}$, Nle$^{27}$, D-Arg$^{28}$, Har$^{29}$]hGH-RH(1-29)NH$_2$ Peptide 26

[PhAc$^0$, D-Arg$^2$, Phe(pCl)$^6$, D-Har$^9$, Abu$^{15}$, Nle$^{27}$, D-Arg$^{28}$, Har$^{29}$]hGH-RH(1-29)NH$_2$ Peptide 27

[PhAc$^0$, D-Arg$^2$, Phe(pCl)$^6$, D-Lys$^9$, Abu$^{15}$, Nle$^{27}$, D-Arg$^{28}$, Har$^{29}$]hGH-RH(1-29)NH$_2$ Peptide 28

[PhAc$^0$, D-Arg$^2$, Phe(pCl)$^6$, D-Orn$^9$, Abu$^{15}$, Nle$^{27}$, D-Arg$^{28}$, Har$^{29}$]hGH-RH(1-29)NH$_2$ Peptide 29

[PhAc$^0$, D-Arg$^2$, Phe(pCl)$^6$, Cit$^9$, Abu$^{15}$, Nle$^{27}$, D-Arg$^{28}$, Har$^{29}$]hGH-RH(1-29)NH$_2$ Peptide 30

Six very prefterred embodiments have the formulae:

PhAc$^0$-Tyr$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Nle$^{27}$-D-Arg$^{28}$-Har$^{29}$-NH$_2$ Peptide 1

IndAc$^0$-Tyr$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 2

PhAc$^0$-Tyr$^1$-D-Arg$^2$-Asp$^3$-Ala$^4$-Ile$^5$-Phe(pCl)$^6$-Thr$^7$-Asn$^8$-Har$^9$-Tyr(Me)$^{10}$-Arg$^{11}$ -Lys$^{12}$- Val$^{13}$-Leu$^{14}$-Abu$^{15}$-Gln$^{16}$-

Leu$^{17}$-Ser$^{18}$-Ala$^{19}$-Arg$^{20}$-Lys$^{21}$-Leu$^{22}$Leu$^{23}$-Gln$^{24}$-Asp$^{25}$-Ile$^{26}$-Nle$^{27}$-D-Arg$^{28}$-Har$^{29}$-NH$_2$ Peptide 3

PhAc$^0$-Tyr$^1$-D-Arg$^2$-Asp$^3$-Ala$^4$-Ile$^5$-Phe(pCl)$^6$-Thr$^7$-Asn$^8$-Arg$^9$-Tyr(Me)$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$Leu$^{22}$-Leu$^{23}$-Gln$^{24}$-Asp$^{25}$-Ile$^{26}$-Nle$^{27}$-D-Arg$^{28}$-Har$^{29}$-NH$_2$ Peptide 6

PhAc$^0$-His$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$Nle$^{27}$-D-Arg$^{28}$-Har$^{29}$-NH$_2$ Peptide 7

Nac$^0$-His$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu$^{14}$-Abu$^{15}$-Gln$^{16}$-Leu$^{17}$-Ser$^{18}$-Ala$^{19}$-Arg$^{20}$-Lys$^{21}$-Leu$^{22}$Leu$^{23}$-Gln$^{24}$-Asp$^{25}$-Ile$^{26}$-Nle$^{27}$-D-Arg$^{28}$-Har$^{29}$-NH$_2$ Peptide 8

Under well-established convention, these may be abbreviated as follows:

[PhAc$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 1

[IndAc$^0$, D-Arg$^2$ Phe(pCl)$^6$, Arg$^9$, Abu$^{15}$, Nle$^{27}$, D-Arg$^{28}$, Har$^{29}$]hGH-RH(1-29)NH$_2$ Peptide 2

[PhAc$^0$, D-Arg$^2$, Phe(pCl)$^6$, Har$^9$, Tyr(Me)$^{10}$, Abu$^{15}$, Nle$^{27}$, D-Arg$^{28}$Har$^{29}$]hGH -RH(1-29)NH$_2$ Peptide 3

[PhAc$^0$, D-Arg$^2$, Phe(pCl)$^6$, Arg$^9$,Tyr(Me)$^{10}$, Abu$^{15}$, Nle$^{27}$, D-Arg$^{28}$, Har$^{29}$]hGH-RH(1-29)NH$_2$ Peptide 6

[PhAc$^0$, His$_1$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 7

[Nac$^0$, His$^1$, D-Arg$^2$, Phe(pCl)$^6$, Arg$^9$, Abu$^{15}$, Nle$^{27}$, D-Arg$^{28}$, Har$^{29}$]hGH-RH(1-29) NH$_2$ Peptide 8

C. Method of Preparation

1. Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, 111, 1984 (2nd. ed.), and M. Bodanszky, "Principles of Peptide Synthesis", Springer Verlag, 1984. The hGH-RH antagonist peptides are preferably prepared using solid phase synthesis, such as that generally described by Merrifield, J.Am.Chem.Soc., 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. The preferred protecting group is Boc.

In solid phase synthesis, the N-alpha-protected amino acid moiety which forms the aminoacyl group of the final peptide at the C-terminus is attached to a polymeric resin support via a chemical link. After completion of the coupling reaction, the alpha amino protecting group is selectively removed to allow subsequent coupling reactions to take place at the amino-terminus, preferably with 50% TFA in DCM when the N-alpha-protecting group is Boc. The remaining amino acids with similarly Boc-protected alpha amino groups are coupled stepwise to the free amino group of the preceding amino acid on the resin to obtain the desired peptide sequence. Because the amino acid residues are coupled to the alpha amino group of the C-terminus residue, growth of the synthetic hGH-RH analogue peptides begins at the C terminus and progresses toward the N-terminus. When the desired sequence has been obtained, the peptide is acylated at the N-terminus, and it is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha amino protecting group prior to the coupling of the next amino acid.

A typical synthesis cycle is shown in Table I.

TABLE I

Protocol for a Typical Synthetic Cycle Using Boc-strategy

| Step | Reagent | Mixing Time (min) |
|---|---|---|
| 1. Deprotection | 50% TFA in DCM | 5 + 25 |
|  | DCM wash | 1 |
|  | 2-propanol wash | 1 |
| 2. Neutralization | 5% DIEA in DCM | 1 |
|  | DCM wash | 1 |
|  | MeOH wash | 1 |
|  | 5% DIEA in DCM | 3 |
|  | MeOH wash | 1 |
|  | DCM wash (3 times) | 1 - 1 |
| 3. Coupling | 3 equiv. Boc-amino acid in DCM or DMF + 3 equiv. DIC or the preformed HOBt ester of the Boc-amino acid | 60 |
|  | MeOH wash | 2 |
|  | DCM wash | 2 |
| 4. Acetylation (if appropriate) | Ac$_2$O in DCM (30%) | 10 + 20 |
|  | MeOH wash (3 times) | 2 |
|  | DCM wash (3 times) | 2 |

After completion of the synthesis, the cleavage of the peptide from the resin can be effected using procedures well known in peptide chemistry.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the reactions used to form the peptides. The following general rules are followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

The reactive side chain functional groups are preferably protected as follows: benzyl for Thr and Ser; 2-bromobenzyloxycarbonyl for Tyr; p-toluene-sulfonyl or nitro for Arg and Har; 2-chlorobenzyloxycarbonyl or fluorenylmethyloxycarbonyl for Lys, Orn; benzyloxymethyl for His; and cyclohexyl or fluorenylmethyl for Asp and Glu. The side chains of Asn and Gln are unprotected.

3. Stepwise Coupling of Amino Acid Residues to the Support Polymer

The hGH-RH antagonist peptides may be synthesized on a variety of support polymers, i.e. MBHA, Merrifield, PAM or Wang resins. When N-alpha-Boc protected amino acids are used for synthesis, the preferred resin is MBHA. In this case, peptides with an amidated C-terminus are obtained uipon cleavage from the support phase.

First, the C-terminal amino acid is attached to the neutralized MBHA resin, and then the subsequent amino acid couplings are carried out. Each protected amino acid is coupled in about a three-fold molar excess, with respect to resin-bound free amino residues, and the coupling may be carried out in a medium such as DMF: $CH_2Cl_2$ (1:1) or in DMF or $CH_2Cl_2$ alone. The selection of an appropriate coupling reagent is within the skill of the art. Particularly suitable as coupling reagents are N,N'-diisopropyl carbodiimide (DIC), or HBTU combined with HOBt. The success of the coupling reaction at each stage of the synthesis is preferably monitored by the ninhydrin reaction. In cases where incomplete coupling occurs, either the coupling procedure is repeated, or the resin-bound unreacted amino residues are acetylated using $Ac_2O$/DCM, before removal of the alpha amino protecting group.

Final acylation of the N-terminus of the peptide is done in the same way as the previous couplings, with the difference that the appropriate carboxylic acid is used instead of an amino acid.

4. Removal of the Peptide from the Support Polymer.

When the synthesis is complete, the peptide is cleaved from the support phase. Removal of the peptide from the resin is performed by treatment with a reagent such as liquid hydrogen fluoride which also cleaves all remaining side chain protecting groups.

Suitably, the dried and protected peptide-resin is treated with a mixture consisting of 1.0 mL m-cresol and 10 mL anhydrous hydrogen fluoride per gram of peptide-resin for 60 min at 0° C. to cleave the peptide from the resin as well as to remove all side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

5. Purification

The purification of the crude peptides can be effected using procedures well known in peptide chemistry. For example, purification may be performed on a MacRabbit HPLC system (Rainin Instrument Co. Inc., Woburn, Mass.) with a Knauer UV Photometer and a Kipp and Zonen BD40 Recorder using a Vydac 218TP5010 reversed-phase column (10×250 mm, packed with C18 silica gel, 300 Å pore size, 5 µm particle size) (The Separations Group Inc., Hesperia, Calif.). The column is eluted with a solvent system consisting of (A) 0.1% aqueous TFA and (B) 0.1% TFA in 70% aqueous MeCN in a linear gradient mode (e.g., 30–55% B in 120 min). The eluent is monitored at 220 nm, and fractions are examined by analytical HPLC using a Hewlett-Packard Model HP-1090 liquid chromatograph and pooled to give maximum purity. Analytical HPLC is carried out on a Vydac 218TP52 reversed-phase column (2×250 mm, C18, 300 Å, 5 µm) using isocratic elution with a solvent system consisting of (A) and (B) defined above. The pealks are monitored at 220 and 280 nm. The peptides are judged to be substantially (>95%) pure by analytical HPLC. The expected amino acid composition is also confirmed by amino acid analysis.

D. Pharmaceutical Composition

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartarate, and the like. Particularly preferred antagonists are salts of low solubility, e.g., pamoate salts and the like. These exhibit long duration of activity.

The compounds of the present invention are suitably administered to subject humans or animals s.c., i.m., or i.v; intranasally or by pulmonary inhalation; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, depot injections, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the mode of administration and the intended result. In general, the dosage range is between 1–100 µg/kg of body weight of the host per day.

E. Therapeutic Uses of GH-RH Antagonists hGH-RH antagonists can be used in treatment of conditions caused by excess growth hormone, for example acromegaly, which is manifested by an abnormal enlargement of the bones of the face and extremities. The GH-RH antagonists may also be used to treat diabetic nephropathy (the main cause of blindness in diabetics) and diabetic retinopathy, in which damage to the eye and kidney respectively is thought to be due to GH.

The hGH-RH antagonists are designed to block the binding and therefore the action of GH-RH, which stimulates the secretion of GH, which in turn stimulates production of IGF-1. GH-RH antagonists may be administered alone or together with somatostatin analogues, a combination which more completely suppresses IGF-I levels. It is advantageous to administer antagonists of GH-RH rather than somatostatin due to the fact that GH-RH antagonists may be utilized in situations where target sites do not have somatostatin receptors.

However, the main applications of GH-RH antagonists are in the field of cancer. This is based on the following considerations: GH-RH antagonists are designed to block the binding and therefore the action of GH-RH, which stimulates the secretion of GH, which in turn stimulates production of insulin-like growth factor I (IGF-I) also called somatomedin-C. The involvement of IGF-I (somatomedin-C) in breast cancer, prostate cancer, colon cancer, bone tumors and other malignancies is well established, and somatostatin analogues alone do not adequately suppress GH and IGF-l levels. A complete suppression of IGF-I levels or secretion is required for a better inhibition of tumor growth. Autocrine production of IGF-I by various tumors could be also under control of GH-RH and might therefore be inhibited by GH-RH antagonists. GH-RH antagonists might also inhibit the production of IGF-I. A more detailed theoretical background of the applications of GH-RH in the field of oncology (cancer) is as follows: The receptors for IGF-I are present in primary human breast cancers, prostate cancers, lung cancers, colon cancers, brain-tumors, pancreatic cancers, and in renal cell carcinomas.

The presence of IGF-I receptors in these tumors appears to be related to malignant transformation and proliferations of these cancers. IGF-I can act as endocrine, paracrine or autocrine growth factor for various human cancers, that is the growth of these neoplasms is dependent on IGF-I. GH-RH antagonists by suppressing GH secretion would lower the production of IGF-I. Since IGF-I stimulates growth of these various neoplasms (cancers), the lowering of circulating IGF-I levels should lead to tumor growth inhibition. It is possible that GH-RH antagonists could also lower paracrine or autocrine production of IGF-I by the tumors, which should also lead to inhibition of cancer proliferation. These views are in accordance with modern concepts of clinical oncology. GH-RH antagonists should be given alone or together with somatostatin analogues and a combination would achieve a more complete suppression of IGF-I levels, elimination of tissue IGF-l levels, e.g., in human osteosarcomas, as well as breast cancer, colon cancer, prostate cancer, and non-small cell lung cancer (non-SCLC).

The advantage of GH-RH antagonists over somatostatin analogues is based on the fact that GH-RH antagonists may be utilized for suppression of tumors which do not have somatostatin receptors, for example human osteogenic sarcomas.

Antagonistic analogs of GH-RH have been shown to suppress growth of various tumors in vivo. This effect is exerted in part through inhibition of the GHRH-GH-IGF-I axis. Nevertheless, autocrine/paracrine control of proliferation by IGF-II is also a major factor in many tumors. Interference with this autocrine growth-stimulating pathway offers an approach to tumor control. Antagonistic analogs of GH-RH, MZ-471 {[Ibu$^0$, Tyr$^1$, D-Arg$^2$, Abu$^{15}$, Nle$^{27}$]hGH-RH(1-28) Agm} and MZ-5–156 {[PhAc$^0$, D-Arg$^2$, Abu$^{15}$, Nle$^{27}$]hGH-RH(1-28) Agm} significantly inhibited the rate of proliferation of mammary (MDA-MB-468, ZR-75-1), prostatic (PC-3 and DU-145), and pancreatic (MiaPaCa-2, SW-1990 and Capan-2) cancer cell lines in vitro as shown by calorimetric and [$^3$H]-thymidine incorporation tests, reduced the expression of IGF-11 mRNA in the cells and the concentration of IGF-II secreted into the culture medium. The same GH-RH antagonists produced similar results in vivo (inhibition of proliferation and reduction of IGF-II production) for prostate tumors (PC-3, DU-145), renal adenocarcinoma (Caki-I) and non-small cell lung carcinoma (H157). These findings suggest that antagonistic analogs of GH-RH can inhibit tumor growth not only by inhibiting the GHRH-GH-IGF-I axis, but also by reducing the IGF-II production in certain tumor cells, thus interrupting its autocrine regulatory pathway.

The present invention is described in connection with the following examples which are set forth for the purposes of illustration only. In the examples, optically active protected amino acids in the L-configuration are used except where specifically noted.

The following Examples set forth suitable methods of synthesizing the novel GH-RH antagonists by the solid-phase technique.

EXAMPLE I

PhAc$^0$-Tyr$^1$-D-Arg$^2$-Asp$^3$-Ala$^4$-Ile$^5$-Phe(pCl)$^6$-Thr$^7$-Asn$^8$-Arg$^9$-Tyr$^{10}$-Arg$^{11}$-Lys$^{12}$-Val$^{13}$-Leu $^{14}$-Abu$^{15}$-Gln$^{16}$-Leu$^{17}$-Ser$^{18}$-Ala$^{19}$-Arg$^{20}$-Lys$^{21}$-Leu$^{22}$-Leu$^{23}$-Gln$^{24}$-Asp$^{25}$-Ile$^{26}$-Nle$^{27}$-D-Arg$^{28}$-Har$^{29}$-NH$_2$ (Peptide 1) {[PhAc$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$}

The synthesis is conducted in a stepwise manner using manual solid phase peptide synthesis equipment. Briefly, para-methylbenzhydrylamine (MBHA) resin (Bachem, California) (720 mg, 0.50 mmole) is neutralized with 5% DIEA in CH$_2$Cl$_2$ and washed according to the protocol described in Table I. The solution of Boc-Har(NO$_2$)-OH (500 mg, 1.5 mmole) in DMF-CH$_2$Cl$_2$ (1:1) is shaken with the neutralized resin and DIC (235 μL, 1.5 mmole) in a manual solid phase peptide synthesis apparatus for 1 hour. After the completion of the coupling reaction is proved by negative ninhydrin test, deprotection with 50% TFA in CH$_2$Cl$_{21}$ and neutralization with 5% DIEA in CH$_2$Cl$_2$, the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(2BrZ)-OH, Boc-Arg(Tos)-OH, Boc-Asn-OH, Boc-Thr(Bzl)-OH, Boc-Phe(pCl)-OH, Boc-Ile-OH, Boc-Ala-OH, Boc-Asp(OcHx)-OH, Boc-D-Arg(Tos)-OH, Boc-Tyr(2BrZ)-OH.

These protected amino acid residues (also commonly available from Bachem Co.) are represented above according to a well accepted con-vention. The suitable protecting group for the side chain functional group of particular amino acids appears in parentheses. The OH groups in the above formulae indicate that each residue's carboxyl terminus is free.

The protected amino acids (1.5 mmole each) are coupled with DIC (235 μL, 1.5 mmole) with the exceptions of Boc-Asn-OH and Boc-Gln-OH which are coupled with their preformed HOBt esters. After removal of the N$^α$-Boc protecting group from Tyr$^1$, the peptide is acylated with phenylacetic acid (PhAc) (272 mg, 2 mmole) using DIC (313, μL, 2 mmole).

In order to cleave the peptide from the resin and deprotect it, the dried peptide resin (2.18 g) is stirred with 2 mL m-cresol and 20 mL hydrogen fluoride (HF) at 0° C. for 1 hour. After evaporation of the HF under vacuum, the remnanit is washed with dry diethyl ether and ethyl acetate.

The cleaved and deprotected peptide is dissolved in 50% acetic acid and separated from the resin by filtration. After dilution with water and lyophilization, 1.51 g crude product is obtained.

The crude peptide is checked by analytical HPLC using a Hewlett-Packard Model HP-1090 liquid chromatograph with a Vydac 218TP52 reversed-phase column (2×250 mm, packed with C18 silica gel, 300 Å pore size, 5 μm particle size) (The Separations Group Inc., Hesperia, Calif.) and linear gradient elution, (e.g., 40–70% B) with a solvent system consisting of (A) 0.1% aqueous TFA and (B) 0.1% TFA in 70% aqueous MeCN. 500 mg of the crude peptide is dissolved in AcOH/H$_2$O, stirred, filtered and applied on a Beckman Ultraprep ODS column (21.2×150 mm, packed with C18 silica gel, 300 Å pore size, 10 μm particle size). The column is eluted with a solvent system described above in a linear gradient 25 mode (e.g., 30–55% B in 120 min); flow rate 6 mL/min. The eluent is monitored at 220 nm, and fractions are examined by analytical HPLC.

Fractions with purity higher than 95% are pooled and lyophilized to give 98 mg pure product. The analytical HPLC is carried out on a Vydac C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electro-spray mass

EXAMPLE II

PhAc⁰-Tyr¹-D-Arg²-Asp³-Ala⁴-Ile⁵-Phe(pCl)⁶-Thr⁷-Asn⁸-Har⁹-Tyr(Me)¹⁰-Arg¹¹-Lys¹²Val¹³Leu¹⁴-Abu¹⁵-Gln¹⁶-Leu¹⁷-Ser¹⁸-Ala¹⁹-Arg²⁰-Lys²¹-Leu²²-Leu²³_Gln²⁴-Asp²⁵-Ile²⁶-Nle²⁷-D-Ar²⁸-Har²⁹-NH₂ (Peptide 3)

{[PhAc⁰, D-Arg², Phe(pCl)⁶, Har⁹, Tyr(Me)¹⁰, Abu¹⁵, Nle²⁷ D-Arg²⁸, Har²⁹]hGH-RH(1-29)NH₂}

The synthesis is conducted in a stepwise manner using manual solid phase peptide synthesis equipment. Briefly, para-methylbenzhydrylamine (MBHA) resin (Bachem, California) (100 mg, 0.070 mmole) is neutralized with 5% DIEA in CH₂Cl₂ and washed according to the protocol described in Table 1. The solution of Boc-Har(NO₂)-OH (83mg, 0.25 mmole) in DMF-CH₂Cl₂ (1:1) is shal<en with the neutralized resin and DIC (44 µL, 0.275 mmole) in a manual solid phase peptide synthesis equipment for 1 hour. After the completion of the coupling reaction is proved by negative ninhydrin test, deprotection with 50% TFA in CH₂Cl₂, and neutralization with 5% DIEA in CH₂Cl₂ the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-Arg(Tos)-OH, Boc-Tyr(Me)-OH, Boc-Har(NO₂)-OH, Boc-Asn-OH, Boc-Thr(Bzl)-OH, Boc-Phe(pCl)-OH, Boc-Ile-OH, Boc-Ala-OH, Boc-Asp(OcHx)-OH, Boc-D-Arg(Tos)-OH, Boc-Tyr(2BrZ)-OH.

These protected amino acid residues (also commonly available from Bachem Co.) are represented above according to a well accepted convention. The suitable protecting group for the side chain functional group of particular amino acids appears in parentheses. The OH groups in the above formulae indicate that each residue's carboxyl terminus is free.

The protected amino acids (0.25 mmole each) are coupled with DIC (44, µL, 0.275 mmole) with the exceptions of Boc-Asn-OH and Boc-Gln-OH which are coupled with their preformed HOBt esters. After removal of the Nᵅ-Boc protecting group from Tyr¹; the peptide is acylated with phenylacetic acid (PhAc) (54 mg, 0.4 mmole) using DIC (70 µL, 0.44 mmole).

In order to cleave the peptide from the resin and deprotect it, the dried peptide resin (206 mg) is stirred with 0.5 mL m-cresol and 5 mL hydrogen fluoride (HF) at 0° C. for 1 hour. After evaporation of the HF under vacuum, the remnant is washed with dry diethyl ether and ethyl acetate. The cleaved and deprotected peptide is dissolved in 50% acetic acid and separated from the resin by filtration. After dilution with water and lyophilization, 112 mg crude product is obtained.

The crude peptide is checked by analytical HPLC using a Hewlett-Packard Model HP-1090 liquid chromatograph with a Vydac 218TP52 reversed-phase column (2×250 mm, packed with C18 silica gel, 300 Å pore size, 5 µm particle size) (The Separations Group Inc., Hesperia, Calif.) and linear gradient elution, (e.g., 40–70% B) with a solvent system consisting of (A) 0.1% aqueous TFA and (B) 0.1% TFA in 70% aqueous MeCN. 80 mg of the crude peptide is dissolved in AcOH/H₂O, stirred, filtered and applied on a Vydac 218TP5010 column (10×250 mm) packed with C8 silica gel. The column is eluted with a solvent system described above in a linear gradient mode (e.g., 30–55% B in 120 min); flow rate 2mL/min. The eluent is monitored at 220 nm, and fractions are examined by analytical HPLC. Fractions with purity higher than 95% are pooled and lyophilized to give 9.6 mg pure product. The analytical HPLC is carried out on a Vydac C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Peptide 2, and Peptides 4 through 30 are synthesized in the same manner as Peptide 1 and Peptide 3, except that these peptides also contain other substitutions, to yield:

[IndAco, D-Arg², Phe(pCl)⁶, Arg⁹, Abu¹⁵, Nle²⁷, D-Arg²⁸, Har²⁹]hGH-RH(1-29)NH₂ Peptide 2

[PhAc⁰, D-Arg², Phe(pCl)⁶, Har⁹, Abu¹⁵, Nle²⁷, D-Arg²⁸, Har²⁹]hGH-RH(1-29)NH₂ Peptide 4

[Nac⁰, D-Arg², Phe(pCl)⁶, Arg⁹, Abu¹⁵, Nle²⁷, D-Arg²⁸, Har²⁹]hGH-RH(1-29)NH₂ Peptide 5

[PhAc⁰, D-Arg², Phe(pCl)⁶, Arg⁹, Tyr(Me)¹⁰, Abu¹⁵, Nle²⁷, D-Arg²⁸, Har²⁹]hGH RH(1-29)NH₂ Peptide 6

[PhAc⁰, His¹, D-Arg², Phe(pCl)⁶, Arg⁹, Abu¹⁵, Nle²⁷, D-Arg²⁸, Har²⁹]hGH-RH(1-29)NH₂ Peptide 7

[Nac⁰, His¹, D-Arg², Phe(pCl)⁶, Arg⁹, Abu¹⁵, Nle²⁷, D-Arg²⁸, Har²⁹]hGH-RH(1-29)NH₂ Peptide 8

[PhAcu⁰, D-Arg², Phe(pCl)⁶, Arg⁹, Abu¹⁵, Nle²⁷, D-Arg²⁹] hGH-RH(1-29)NH₂ Peptide 9

[PhAc⁰, D-Arg², Phe(pCl)⁶, Abu¹⁵, Arg¹⁶, Nle²⁷, D-Arg²⁹] hGH-RH(1-29)NH₂ Peptide 10

[PhAc⁰, D-Arg², Phe(pCl)⁶, Abu¹⁵, Nle²⁷, D-Arg²⁸, Har²⁹] hGH-RH(1-29)NH₂Peptide 11

[PhAc⁰, D-Arg², Phe(pCl)⁶, Nle⁹, Abu¹⁵, Nle²⁷, D-Arg²⁹] hGH-RH(1-29) NH₂ Peptide 12

[PhAc⁰, D-Arg², Phe(pCl)⁶, Nle¹³, Nle¹⁴ᐟ ᴬᵇᵘ¹⁵, Nle²⁷, D-Arg²⁹]hGH-RH(1- 29)NH₂ Peptide 13

[PhAc⁰, D-Arg², Phe(pCl)⁶, Nle¹⁵, Nle²⁷, D-Arg²⁹]hGH-RH (1-29)NH₂ Peptide 14

[PhAc⁰, D-Arg², Phe(pCl)⁶, Abu¹⁵, Nle⁸, Nle²⁷₁, D-Arg²⁹] hGH-RH(1-29) NH₂ Peptide 15

[PhAc⁰, D-Arg², Phe(pCl)⁶, Tyr(Me)¹⁰, Abu¹⁵, Nle²⁷, D-Arg²⁹]hGH-RH(1-29)NH₂ Peptide 16

[PhAc⁰, D-Arg², Phe(pCl)⁶, Abu⁸, Tyr(Me)¹⁰, Abu¹⁵, Nle²⁷, D-Arg²⁹]hGH-RH(1-29)NH₂ Peptide 17

[PhAcu⁰, D-Arg², Phe(pCl)⁶, D-Abu⁸, Tyr(Me)¹⁰, Abu¹⁵, Nle²⁷, D-Arg²⁹]hGH-RH (1-29)NH₂ Peptide 18

[PhAc⁰, D-Arg², Phe(pCl)⁶, Tyr(Me)¹⁰, Abu¹⁵, D-Arg²⁷, Arg²⁸, D-Arg²⁹]hGH-RH (1-29)NH₂ Peptide 19

[PhAc⁰, D-Arg², Phe(pCl)⁶, Tyr(Me)⁶, Abu¹⁵₁, D-Arg²⁷, Arg²⁸₁, D-Arg²⁹]hGH-RH (1-29)NH₂ Peptide 20

[PhAc⁰, D-Arg², Phe(pCl)⁶, Abu¹⁵, D-Arg²⁷, Arg²⁸, D-Arg²⁹]hGH-RH(1-29) NH₂ Peptide 21

[PhAc⁰, D-Arg², Phe(pCl)⁶, Abu⁸, Tyr(Me)¹⁰, Abu¹⁵, D-Arg²⁷, Arg²⁸, D-Arg²⁹]hGH-RH(1-29)NH₂ Peptide 22

[PhAc⁰, D-Arg², Phe(pCl)⁶, D-Abu⁸, Tyr(Me)¹⁰, Abu¹⁵, D-Arg²⁷, Arg²⁸, D-Arg²⁹]hGH-RH(1-29)NH₂ Peptide 23

[PhAc⁰, D-Arg², Phe(pCl)⁶, Lys⁹, Abu¹⁵, Nle²⁷, D-Arg²⁸, Har²⁹]hGH-RH(1-29)NH₂ Peptide 24

[PhAc⁰, D-Arg², Phe(pCl)⁶, Orn⁹, Abu¹⁵, Nle²⁷, D-Arg²⁸, Har²⁹]hGH-RH(1-29)NH₂ Peptide 25

[PhAc⁰, D-Arg², Phe(pCl)⁶, D-Arg⁹, Abu¹⁵, Nle²⁷, D-Arg²⁸, Har²⁹]hGH-RH(1-29)NH₂ Peptide 26

[PhAc⁰, D-Arg², Phe(pCl)⁶, D-Har⁹, Abu¹⁵, Nle²⁷₁, D-Arg²⁸, Har²⁹]hGH-RH(1-29)NH₂ Peptide 27

[PhAc⁰, D-Arg², Phe(pCl)⁶, D-Lys⁹, Abu¹⁵, Nle²⁷, D-Arg²⁸, Har²⁹]hGH-RH(1-29)NH₂ Peptide 28

[PhAc⁰, D-Arg², Phe(pCl)⁶, D-Orn⁹, Abu¹⁵, Nle²⁷, D-Arg²⁸, Har²⁹]hGH-RH(1-29)NH₂ Peptide 29

[PhAc⁰, D-Arg², Phe(pCl)⁶, Cit⁹, Abu¹⁵, Nle²⁷, D-Arg²⁸, Har²⁹]hGH-RH(1-29)NH₂ Peptide 30

EXAMPLE III

Biological Activity

The peptides of the present invention were tested in in vitro and in vivo assays for their ability to inhibit the hGH-RH(1-29)NH₂ induced GH release.

Superfused Rat Pituitary System

The analogs were tested in vitro in a test described earlier (S. Vigh and A. V. Schally, Peptides 5:241–347, 1984) with modification (Z. Rekasi and A. V. Schally, P.N.A.S. 90:2146–2149, 1993).

Briefly, the cells are preincubated with peptides for 9 minutes (3mL) at various concentrations. Immediately after the incubation, 1 nM hGH-RH(1-29)NH₂ is administered for 3 minutes (1 mL) [0 minute response]. To check the duration of the antagonistic effect of the analogue, 1 nM hGH-RH(1-29)NH₂ is applied 30, 60, 90, and 120 minutes later for 3 minutes [30, 60, 90, 120 min responses]. Net integral values of the GH responses are evaluated. GH responses are compared to and expressed as percent of the original GH response induced by 1 nM GH-RH(1-29)NH₂. The effect of the new antagonists are compared to that of [Ac-Tyr¹,D-Arg²]hGH-RH(1-29)NH₂, the "Standard antagonist".

Growth Hormone Radio-immunoassay

Rat GH levels in aliquots of undiluted and diluted superfusion samples were measured by double-antibody radioimmunoassay using materials supplied by the National Hormone and Pituitary Program, Baltimore, Md. The results of RIA were analyzed with a computer program developed in our institute (V. Csernus and A. V. Schally, in Neuroendocrine Research Methods, Harwood Academic (Greenstein, B. D. ed., London, pp. 71–109, 1991), hereby incorporated by reference. Inter-assay variation was less than 15% and intra-assay variation was less than 10%.

GH-RH Binding Assay. A sensitive radioreceptor binding assay was developed to determine the binding characteristics of the antagonists of GH-RH (G. Halmos, A. V. Schally et al., *Receptor* 3, 87–97, 1993), hereby incorporated by reference. The assay is based on binding of labelled [His¹, Nle²⁷]hGH-RH(1-32)NH₂ to rat anterior pituitary membrane homogenates. Iodinated derivatives of [His¹, Nle²⁷] hGH-RH(1-32)NH₂ are prepared by the chloramine-T method (F. C. Greenwood et al., *Biochemistry* 89:114–123, 1963), hereby incorporated by reference. Pituitaries from male Sprague-Dawley rats (250–300 g) are used to prepare crude membranes. For saturation binding analyses, membrane homogenates are incubated with at least 6 concentrations of [His¹, ¹²⁵I-Tyr¹⁰,Nle²⁷]hGH-RH(1-32) NH₂, ranging from 0.005 to 0.35 nM in the presence or absence of excess unlabelled peptide (1 μM).

The pellet is counted for radioactivity in a γ-counter. The affinities of the antagonist peptides tested to rat pituitary GH-RH receptors are determined in competitive binding experiments. The final binding affinities are estimated by $K_i$ (dissociation constant of the inhibitor-receptor complex) and are determined by the Ligand PC and McPherson computer programs of Munson and Rodbard (P. J. Munson and D. Rodbard, *Anal. Biochem.* 107, 220–239, 1980). Relative affinities compared to [Ac-Tyr¹,D-Arg²]hGH-RH(1-29) NH₂, the Standard antagonist, are calculated as the ratio of $K_i$ of the tested GH-RH antagonist to the $K_i$ of the Standard antagonist.

In Vivo Tests

GH-RH antagonistic effect of the analogs was tested on young male Sprague-Dawley rats (200–250 g). In each experiment, 5 groups of 7 animals each were used. The compounds (80 μg/kg) and GH-RH(1-29)NH₂ (3 μg/kg) were dissolved in 5.5% mannitol and given intravenously to the jugular vein of the rats under Nembutal anesthesia. The time elapsed between the administrations of the antagonist and GH-RH varied between groups, according to the following schedule. The first group of animals received GH-RH injection 5 min after the administration of the antagonist; for the second, third and fourth group of animals, the time interval elapsed between the injection of the antagonist and that of GH-RH was 15, 30, and 60 min, respectively. The control group was first injected with the solvent alone instead of the antagonist, followed by a GH-RH injection 5 min later.

0.4 mL blood samples were taken for GH RIA before the administration of the antagonist ("blood0"), and 5 min after the injection of GH-RH ("blood1"). The GH response in each group was calculated as $rGH=(GH_{blood1}/GH_{blood0})$ mean±S.E.M. of the individual differences. Relative inhibition of GH response (%) in each group treated was calculated as $100\times(rGH_{treated}-1)/(rGH_{control}-1)$ Results in Vitro The results of the in vitro antagonistic activities tested in superfused rat pituitary system and binding assay are summarized in Table II and Table III, respectively. As it can be seen from these data, the substitutions present in the molecules cause an immense increase in receptor binding as well as in inhibition of GH release in vitro as compared to the standard antagonist. The most potent antagonist in vitro, Peptide 1, caused a complete inhibition of the GH-RH induced GH release for 90 min, under the standard test conditions. The first sign of the recovery of the GH-RH responsiveness was detected 120 min after the exposure to this analog.

TABLE II

Inhibition of GH Release in Superfused Rat Pituitary System

| Antagonist | Dose (nM) | Inhibition of GH release (%) | | | | |
|---|---|---|---|---|---|---|
| | | 0 min | 30 min | 60 min | 90 min | 120 min |
| Standard antagonist: | 100 | 62.1 | 2.5 | 19 | | |
| Peptide 1 | 30 | 100 | 100 | 100 | 100 | 94 |
| Peptide 2 | 30 | 100 | 100 | 100 | 100 | 91 |
| Peptide 3 | 30 | 85 | 98 | 91 | 92 | 87 |
| Peptide 4 | 30 | 83 | 86 | 80 | 79 | 68 |
| Peptide 5 | 30 | 79 | 77 | 59 | 58 | 50 |
| Peptide 6 | 30 | 93 | 93 | 97 | 95 | 90 |
| Peptide 7 | 30 | 97 | 92 | 82 | 77 | 65 |
| Peptide 8 | 30 | 100 | 100 | 98 | 97 | 90 |
| Peptide 9 | 30 | 91 | 87 | 79 | 72 | 59 |
| Peptide 10 | 30 | 75 | 69 | 46 | 24 | 22 |
| Peptide 11 | 30 | 96 | 89 | 80 | 56 | 42 |
| Peptide 12 | 30 | 68 | 75 | 48 | 52 | 52 |
| Peptide 16 | 30 | 65 | 87 | 83 | 56 | 65 |
| Peptide 19 | 30 | 58 | 47 | 59 | 23 | 39 |

TABLE III $K_i$ Values and Relative Affinities (R.A) of hGH-RH Antagonists

| Peptide | $K_i$ (nM) | R.A. |
|---|---|---|
| Standard | 2.94 | 1 |
| Peptide 1 | 0.044 | 67 |
| Peptide 2 | 0.046 | 64 |
| Peptide 3 | 0.068 | 43 |
| Peptide 4 | 0.087 | 34 |
| Peptide 5 | 0.036 | 82 |

TABLE III-continued

K$_i$ Values and Relative Affinities (R.A) of hGH-RH Antagonists

| Peptide | K$_i$ (nM) | R.A. |
|---|---|---|
| Peptide 9 | 0.058 | 51 |
| Peptide 10 | 0.107 | 27 |
| Peptide 11 | 0.071 | 41 |
| Peptide 12 | 0.070 | 42 |
| Peptide 16 | 0.070 | 42 |

Results in Vivo

Table IV shows the serum GH responses and their relative inhibitions in rats pretreated with GH-RH antagonists. All of the tested analogs (Peptide 1, Peptide 2, Peptide 3, Peptide 4, Peptide 8, Peptide 9, Peptide 11, and Peptide 1 6) produce strong and long-lasting inhibition of the GH release stimulated by hGH-RH(1-29)NH$_2$. Peptide 1 and Peptide 2 are the most potent on the short term, inhibiting GH response by 95% and 91%, when given 5 min before the hGH-RH(1-29)NH$_2$. The effect of these two peptides lasts for at least 30 min. On the other hand, peptides Peptide 11 and Peptide 3, which are slightly less potent on the short term, are extremely long-acting: their effect persists for at least 60 min.

TABLE IV

Serum GH Responses and Relative Inhibitions of GH Responses in Rats Pretreated with GH-RH Antagonists at Different Time Intervals Prior to hGH-RH(1-29)NH$_2$ Administration

| Antagonist | Time interval (min) | GH response mean ± S.E.M. | Relative inhibition % |
|---|---|---|---|
| Peptide 1 | 5 | 1.13 ± 0.13 | 95 |
| | 15 | 1.87 ± 0.13 | 68 |
| | 30 | 1.97 ± 0.16 | 64 |
| | 60 | 3.89 ± 0.65 | −8 |
| | control | 3.68 ± 0.78 | 0 |
| Peptide 2 | 5 | 1.40 ± 0.29 | 91 |
| | 15 | 3.45 ± 0.13 | 45 |
| | 30 | 3.64 ± 0.71 | 41 |
| | 60 | 5.41 ± 1.35 | 2 |
| | control | 5.47 ± 0.97 | 0 |
| Peptide 3 | 5 | 3.01 ± 0.41 | 68 |
| | 15 | 3.63 ± 0.80 | 61 |
| | 30 | 4.89 ± 0.95 | 41 |
| | 60 | 5.36 ± 0.63 | 34 |
| | control | 7.65 ± 0.66 | 0 |
| Peptide 4 | 5 | 3.08 ± 0.58 | 82 |
| | 15 | 7.73 ± 1.12 | 43 |
| | 30 | 12.00 ± 2.54 | 7 |
| | 60 | 11.88 ± 0.90 | 8 |
| | control | 12.82 ± 1.38 | 0 |
| Peptide 8 | 5 | 2.3 ± 0.3 | 74 |
| | 15 | 3.6 ± 0.4 | 46 |
| | 30 | 5.5 ± 0.6 | 8 |
| | 60 | 5.8 ± 0.7 | 1 |
| | control | 5.8 ± 0.5 | 0 |
| Peptide 9 | 5 | 2.75 ± 0.75 | 75 |
| | 15 | 3.85 ± 0.50 | 59 |
| | 30 | 3.34 ± 0.30 | 67 |
| | 60 | 7.32 ± 1.16 | 10 |
| Peptide 11 | 5 | 5.15 ± 1.11 | 84 |
| | 15 | 13.64 ± 1.41 | 50 |
| | 30 | 16.04 ± 4.36 | 40 |
| | 60 | 16.61 ± 6.02 | 38 |
| | control | 26.17 ± 3.92 | 0 |
| Peptide 16 | 5 | 2.89 ± 0.65 | 77 |
| | 15 | 3.44 ± 0.62 | 70 |
| | 30 | 5.24 ± 1.36 | 48 |
| | 60 | 9.19 ± 1.89 | 0 |
| | control | 9.13 ± 1.69 | 0 |

EXAMPLE IV

Oncological Tests

Antitumor activities of the peptides of the present invention were tested in various cancer models. The antitumor effects of these new peptides were compared with those of earlier analogs (MZ-4-71 and MZ-5-156, subject to U.S. Pat. No. 5,550,212 and U.S. patent application Ser. No. 08/642,472.

Effect of GH-RH Antagonists on MXT Mouse Mammary Tumors

Estrogen independent MXT tumors were transplanted sc. to female BDF mice. One day after transplantation, the mice were divided into groups of 10 animals each, and the treatment was started. The mice in groups 1, 2, 3, and 4 received single injections daily of various GH-RH antagonists sc. at 20 μg dose per day for 18 days. In groups 5 and 6, the peptides were administered by Alzet osmotic pumps releasing a daily amount of 20 μg peptide. Tumors were measured regularly, and tumor volume was calculated. The mice were sacrificed on day 18 and tumor weights were measured.

Results

Peptides Peptide 1 and Peptide 3 had similar strong inhibitory effect on MXT mouse mammary cancers. Treatment with MZ-5-156 also resulted in a significant inhibition of tumor growth, but its effect was weaker than that of Peptide 1 or Peptide 3 (see Table V and FIG. 1).

TABLE V

Effect of Treatment with GH-RH Antagonists on MXT Mouse Mammary Tumors

| Group | Tumor volume (mm$^3$) | | Tumor weights | Number of surviving |
|---|---|---|---|---|
| | On day 14 | On day 18 | (mg) | mice |
| 1. Control | 4051 ± 1007 | 7040 ± 646 | 7269 ± 292 | 5 |
| 2. MZ-5-156 | 2717 ± 773 | 5368 ± 408* | 4885 ± 480* | 4 |
| 3. Peptide 1 daily inj. | 2924 ± 654 | 4373 ± 381** | 6964 ± 676 | 6 |
| 4. Peptide 3 daily inj. | 1902 ± 349** | 3465 ± 607** | 5266 ± 906 | 8 |
| 5. Peptide 1 pump | 1329 ± 327** | 3403 ± 584** | 4810 ± 645* | 7 |
| 6. Peptide 3 pump | 1688 ± 220** | 4272 ± 295** | 5939 ± 453 | 8 |

*p < 0.05
**p < 0.01

Effect of GH-RH Antagonists on MDA-MB-468 Human Breast Cancer Xenografts in Nude Mice Nude mice bearing MDA-MB-468 hormone-independent human breast cancer xenografts were divided into groups of 10 animals each. The treated groups received single daily s.c. injections of 20 μg of GH-RH antagonists. One group was treated with Peptide 1, a second group was treated with MZ-5-156 for comparison. The control group was injected with the vehicle solvent. The treatment was continued for 5 weeks. Tumors were measured once a week and tumor volume was calculated. The mice were sacrificed at the end of experiment and tumor weights were measured.

Results

Both peptides exerted significant tumor-inhibitory effects on MDA-MB-468 xenografts. In the group injected with Peptide 1, 4 tumors showed constant regression during the experiment. Likewise, MZ-5-156 caused regression of 3 tumors. After 5 weeks of treatment these cancers regressed to small scar-like tissue remnants. Histological examination of these tissues revealed undifferentiated epithelial tumors with extensive necrosis and only a narrow marginal line of living tumor tissue. In contrast, all tumors in the control animals progressed steadily. Final tumor volume and weight in the treated groups were significantly reduced (see Table VI and FIG. II), Peptide 1 having a stronger effect.

TABLE VI

Effect of Treatment with GH-RH Antagonists on MDA-MB-468 Human Breast Cancer Xenografts in Nude Mice

| Group | Final tumor volume ($mm^3$) | Tumor weight (mg) | Number of regressed tumors |
|---|---|---|---|
| Control | 477.5 ± 41.2 | 440.7 ± 37.7 | 0 |
| Peptide 1 | 82.4 ± 29.1** | 64.0 ± 28.7** | 4 |
| MZ-5-156 | 104.4 ± 32.2** | 77.7 ± 31.7** | 3 |

*$p < 0.05$
**$p < 0.01$

Effect of GH-RH Antagonists on HT-29 Human Colon Cancer Xenografts in Nude Mice

HT-29 human colon cancers were transplanted sc. into male nude mice. 19 days after transplantation, the mice were divided into groups of 10 animals each, and the treatment was started. The mice received single daily injections of various GH-RH antagonists sc. at 20 μg dose per day for 6 weeks. Tumors were measured regularly, and tumor volume was calculated. The mice were sacrificed at the end of experiment and tumor weights were measured.

Results

Peptides Peptide 1 and MZ-5-156 had equally strong inhibitory effect on HT-29 human colon cancers. Treatment with Peptide 9 resulted in a smaller but still significant inhibition of tumor growth. Peptide 11 and MZ-4-71 had only little nonsignificant effect. (The results are summarized in Table VII and FIG. III).

TABLE VII

Effect of Treatment with GH-RH Antagonists on HT-29 Human Colon Cancer Xenografts in Nude Mice

| Group | Final tumor volume ($mm^3$) | Tumor weight (mg) |
|---|---|---|
| Control | 2117 ± 751 | 2364 ± 835 |
| MZ-4-71 | 1953 ± 400 | 2189 ± 458 |
| MZ-5-156 | 908 ± 195* | 1012 ± 174* |
| Peptide 11 | 1663 ± 610 | 1849 ± 681 |
| Peptide 9 | 1194 ± 506* | 1383 ± 576* |
| Peptide 1 | 890 ± 322* | 1354 ± 480* |

*$p < 0.05$

Effect of GH-RH antagonist Peptide 1 on U87MG human glioblastoma xenografts in nude mice Mice were implanted s.c. with U87MG glioblastomas and when tumors reached a volume of approx. 70 $mm^3$ the mice were randomly divided into 2 experimental groups. One group was treated with Peptide 1 in single daily s.c. injections of 20 μg for 28 days, while the other group served as control.

Results

Treatment with Peptide 1 inhibited the tumor growth by 77% versus the control group, after 4 weeks of treatment (see Table VIII and FIG. IV).

TABLE VIII

Effect of Treatment with GH-RH Antagonist Peptide 1 on U87MG Human Glioblastoma Xenografts in Nude Mice

| Group | Final tumor volume ($mm^3$) | Tumor weight (g) |
|---|---|---|
| Control | 3425 ± 723 | 4.7 ± 1.3 |
| Peptide 1 | 817 ± 323** | 1.4 ± 0.7** |

**$p < 0.01$

Effect of GH-RH antagonists on PC-3 human prostate cancer xenografts in nude mice Male nude mice were implanted s.c. with 3 $mm^3$ pieces of PC-3 human hormone-independent prostate cancer tissue into both flanks. When tumors reached a volume of approx. 40–50 $mm^3$ the mice were divided into 3 experimental groups. The first and second groups were treated with peptides Peptide 3 and MZ-5-1 56, respectively, in single daily s.c. injections of 20 μg for 21 days, while the third group served as control. Tumor volumes were measured at weekly intervals, tumor weights were measured at the end of experiment.

Results

Both GH-RH antagonists inhibited growth of PC-3 tumors (see Table IX and FIG. V). Peptide 3 exerted stronger growth inhibition (65% inhibition in tumor volume and 62% in tumor weight) than MZ-5-156 (52% and 46%, respectively).

TABLE IX

Effect of Treatment with GH-RH Antagonists on PC-3 Human Prostate Cancer Xenografts in Nude Mice

| Group | Final tumor volume ($mm^3$) | Tumor weight (mg) |
|---|---|---|
| Control | 307.9 ± 64.5 | 191.8 ± 42.6 |
| Peptide 3 | 107.9 ± 12.5* | 73.7 ± 11.9* |
| MZ-5-156 | 148.9 ± 41 | 104.3 ± 27.2 |

*$p < 0.05$

We claim:

1. A peptide selected from the group having the formulae: X-$R^1$-$R^2$-Asp-Ala-$R^5$-$R^6$-Thr-$R^8$-$R^9$-$R^{10}$-Arg-$R^{12}$-$R^{13}$-$R^{14}$-$R^{15}$-$R^{16}$-Leu-$R^{18}$-$R^{19}$-Arg-$R^{21}$-$R^{22}$-Leu-Gln-Asp-Ile-$R^{27}$-$R^{28}$-$R^{29}$-$NH_2$ wherein X is PhAc, IndAc, or Nac,
$R^1$ is Tyr or His,
$R^2$ is D-Arg,
$R^5$ is Ile or Val,
$R^6$ is Phe, or Phe(CI)
$R^8$ is Asn, Gin, Ala,or D-Asn,
$R^9$ is Arg, Har, Lys, Orn, D-Arg, D-Har, D-Lys, D-Om, Cit, Nle, Tyr (Me), Ser, Ala or Aib
$R^{10}$ is Tyr or Tyr(Me),
$R^{12}$ is Lys,
$R^{13}$ is Val or Nle,
$R^{14}$ is Leu or Nle,
$R^{15}$ is Gly, Ala, Abu, Nle or Gln,
$R^{16}$ is Gln or Arg,
$R^{18}$ is Ser or Nle,
$R^{19}$ is Ala,
$R^{21}$ is Lys,
$R^{22}$ is Leu, Ala or Aib,
$R^{27}$ is Met, Leu, Nle, Abu, or D-Arg,
$R^{28}$ is Arg, D-Arg,or Ser,
$R^{29}$ is Arg, D-Arg, Har or D-Har,
Provided that where $R^9$ and $R^{28}$ are Ser, $R^{29}$ is other than Arg or Har and pharmaceutically acceptable salts thereof.

2. A compound of claim 1 selected from the group consisting of

[PhAc$^0$, D-Arg$^2$, Phe(pCl)$^6$, Arg$^9$, Abu$^{15}$, Nle$^{27}$ D-Arg$^{28}$, Har$^{29}$]hGH-RH(1-29) NH$_2$ Peptide 1

[IndAc$^0$, D-Arg$^2$, Phe(pCl)$^6$, Arg$^9$, Abu$^{15,}$ Nle$^{27}$, D-Arg$^{28}$, Har$^{29}$]hGH-RH(1-29)NH$_2$ Peptide 2

[PhAc$^0$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NH$_2$ Peptide 3

[PhAc$^0$, D-Arg$^2$, Phe(pCl)$^6$, Arg$^9$, Tyr(Me)$^{10}$, Abu$^{15}$, Nle$^{27}$, D-Arg$^{28}$, Har$^{29}$]hGH-RH(1-29)NH$_2$ Peptide 6

[PhAc$^0$, His$^1$, D-Arg$^2$, Phe(pCl)$^6$, Arg$^9$, Abu$^{15}$, Nle$^{27}$, D-Arg$^{28}$, Har$^{29}$]hGH-RH)1-29)NH$_2$ Peptide 7

[Nac$^0$, His$^{b1}$, D-Arg$^2$, Phe(pCl)$^6$, Arg$^9$, Abu$^{15}$, Nle$^{27}$, D-Arg$^{28}$, Har$^{29}$]hGH-RH(1-29)NH Peptide 8.

3. A compound of claim 1 having the formula [PhAc$^0$, D-Arg$^2$, Phe(pCl)$^6$, Arg$^9$, Abu$^{15}$, Nle$^{27}$, D-Arg$^{28}$, Har$^{29}$]hGH-RH(1-29)NH$_2$ Peptide 1.

4. A compound of claim 1 having the formula [IndAc$^0$, D-Arg$^2$, Phe(pCl)$^6$, Arg$^9$, Abu$^{15}$, D-Arg$^{28}$, Har$^{29}$]hGH-RH(1-29)NH$_2$ Peptide 2.

5. A compound of claim 1 having the formula [PhAc$^0$, D-Arg$^2$, Phe(pCl)$^6$, Har$^9$, Tyr(Me)$^{10}$, Abu$^{15}$, Nle$^{27}$, D-Arg$^{28}$, Har$^{29}$]hGH-RH(1-29)NH$_2$ Peptide 3.

6. A compound of claim 1 having the formula [PhAc$^0$, D-Arg$^2$, Phe(pCl)$^6$, Arg$^9$, Tyr(Me)$^{10}$, Abu$^{15}$, Nle$^{27}$, D-Arg$^{28}$, Har$^{29}$]hGH-RH(1-29)NH$_2$ Peptide 6.

7. A compound of claim 1 having the formula [PhAc$^0$, His$^1$, D-Arg$^2$, Phe(pCl)$^6$, Arg$^9$ Abu$^{15}$, Nle$^{27}$, D-Arg$^{28}$, Har$^{29}$]hGH-RH(1 -29)NH$_2$ Peptide 7.

8. A compound of claim 1 having the formula [Nac$^0$, His$^1$, D-Arg$^2$, Phe(pCl)$^6$, Arg$^9$, Abu$^{15}$, Nle$^{27}$, D-Arg$^{28}$, Har29] hGH-RH(1-29)NH$_2$ Peptide8.

* * * * *